US009616245B2

(12) United States Patent
Kumar

(10) Patent No.: US 9,616,245 B2
(45) Date of Patent: Apr. 11, 2017

(54) METHOD OF TREATING CELLS WITH DRUG AND RADIATION ACCORDING TO PROTON DENSITY

(76) Inventor: Rajah Vijay Kumar, Karnataka (IN)

( * ) Notice: Subject to any disclaimer, the term of this patent is extended or adjusted under 35 U.S.C. 154(b) by 109 days.

(21) Appl. No.: 13/256,793
(22) PCT Filed: Mar. 16, 2009
(86) PCT No.: PCT/IN2009/000179
§ 371 (c)(1),
(2), (4) Date: Sep. 15, 2011
(87) PCT Pub. No.: WO2010/106544
PCT Pub. Date: Sep. 23, 2010

(65) Prior Publication Data
US 2012/0004591 A1 Jan. 5, 2012

(51) Int. Cl.
*A61N 1/40* (2006.01)
*C12N 13/00* (2006.01)
(Continued)

(52) U.S. Cl.
CPC ............... *A61N 1/40* (2013.01); *A61N 2/004* (2013.01); *C12N 13/00* (2013.01); *A61N 1/327* (2013.01)

(58) Field of Classification Search
CPC .......... A61N 2007/0073; A61N 1/0424; A61N 1/0476; A61N 1/325; A61N 1/327
(Continued)

(56) References Cited

U.S. PATENT DOCUMENTS 4,106,488 A * 8/1978 Gordon ..................... 424/1.37
5,087,616 A * 2/1992 Myers et al. ............... 514/7.6
(Continued)

FOREIGN PATENT DOCUMENTS

WO    WO 2005/120171 A2    12/2005

OTHER PUBLICATIONS

Antoch et al. Whole-body dual-modality PET/CT and whole-body MRI for tumor staging oncology, JAMA Dec. 2003; vol. 290, No. 224. p. 3199.*
(Continued)

*Primary Examiner* — Bhisma Mehta
*Assistant Examiner* — Matthew A Engel
(74) *Attorney, Agent, or Firm* — Laurence P. Colton; Smith Tempel Blaha LLC

(57) ABSTRACT

This Invention relates to a method for achieving Focused Resonance Nanopermeabilization (FORN), which can be utilized in a novel anticancer therapy, and other selective permeabilization therapy and a machine to carryout the said method, where the transient permeabilization of cells by Focused Resonance pulses induces a significant increase of anti-tumor drug concentration in tumor or other interested cells. This invention can be successfully applied to the treatment of tumors in humans and Animals by using antimitotic drugs, chemotherapy. The invention is also useful in transpermeabilization of drug molecules for non cancer applications like vaccine and delivery of genetic materials for therapeutic purposes. Focused Resonance Nanopermeabilization (FORN), would enable a practical solution to a whole body application in its natural environment, without implanting electrodes or external probes, FORN is completely non-invasive. This invention also relates to an apparatus for carrying out the above method.

5 Claims, 8 Drawing Sheets

(51) Int. Cl.
*A61N 1/32* (2006.01)
*A61N 2/00* (2006.01)

(58) Field of Classification Search
USPC ............... 604/2, 22; 435/461; 600/410, 431
See application file for complete search history.

(56) References Cited

U.S. PATENT DOCUMENTS

| | | | |
|---|---|---|---|
| 6,314,316 B1* | 11/2001 | Gilbert et al. | 604/20 |
| 6,562,318 B1* | 5/2003 | Filler | 424/1.29 |
| 6,937,890 B2 | 8/2005 | Jaroszeski et al. | |
| 6,974,415 B2* | 12/2005 | Cerwin et al. | 600/437 |
| 7,109,034 B2 | 9/2006 | Orwar et al. | |
| 7,306,940 B2 | 12/2007 | Miklavic et al. | |
| 7,395,112 B2 | 7/2008 | Keisari et al. | |
| 7,532,008 B2* | 5/2009 | Pendry et al. | 324/318 |
| 2003/0028071 A1* | 2/2003 | Handy et al. | 600/12 |
| 2004/0101969 A1* | 5/2004 | Viglianti | A61B 5/055 436/173 |
| 2004/0236217 A1* | 11/2004 | Cerwin et al. | 600/437 |
| 2007/0208249 A1* | 9/2007 | Kumar | 600/410 |

OTHER PUBLICATIONS

Huber et al. A new noninvasive approach to breast cancer therapy using magnetic resonance imaging-guided focused ultrasound surgery, Cancer Research, 2001; 61: 8441-8447.*
Jordan et al., Effect of Pulsed, High-Power Radiofrequency Radiation on Electroporation of Mammalian Cells, IEEE Transactions on Plasma Science, vol. 32, No. 4, Aug. 2004.*
Moffat et al. A novel polyacrylamide magnetic nanoparticle contrast agent for molecular imaging using MRI, Molecular Imaging, vol. 2, Oct. 2003, pp. 324-332.*
Andrea D'Ariano, "Improving real-time train dispatching models, algorithms and applications," TRAIL Thesis series No. T2008/6, The Netherlands Trail Research School (240 pages) "2008".
C. Sugapriya, et al., "Determining a common production cycle time for an EPQ model with non-instantaneous deteriorating items allowing price discount using permissible delay in payments," ARPN Journal of Engineering and Applied Sciences, vol. 3. No. 2, Apr. 2008 (pp. 26-30).
P. Mishra, et al., "Inventory management of time dependent deteriorating items with salvage value," Applied Mathamatical Sciences, vol. 2, 2008, No. 16, (pp. 793-798).

* cited by examiner

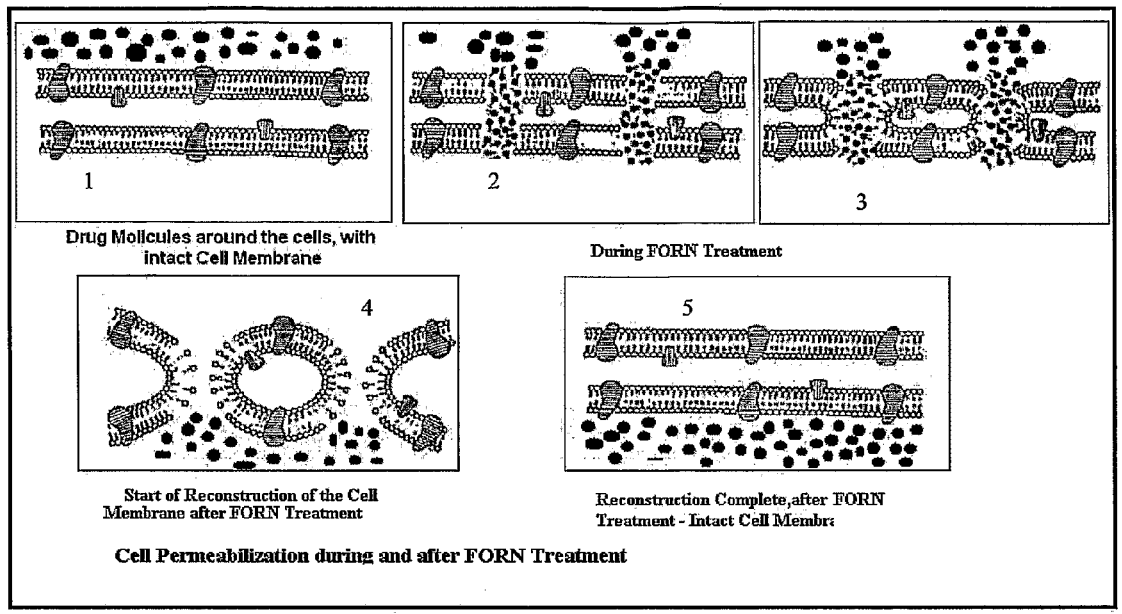
FIGURE: 1
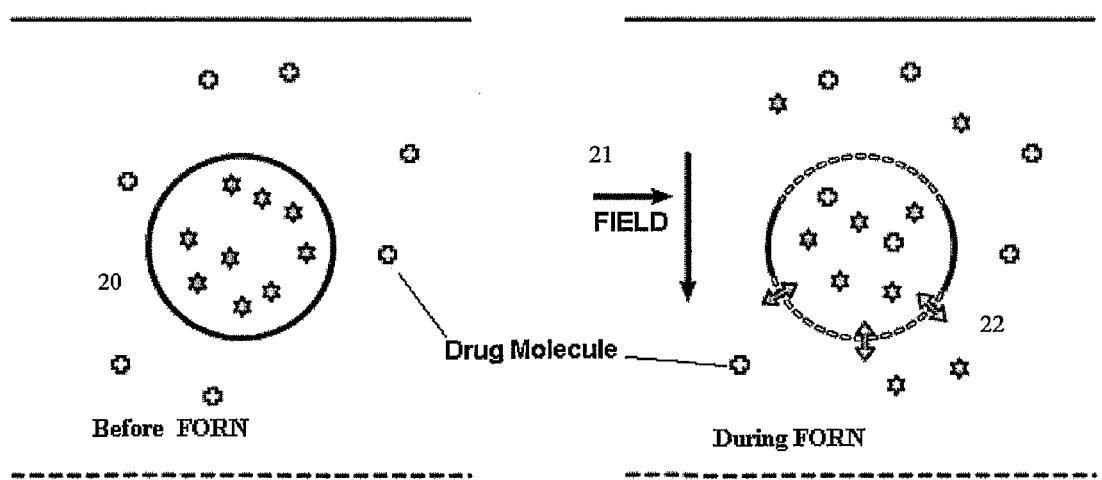
FIGURE: 2

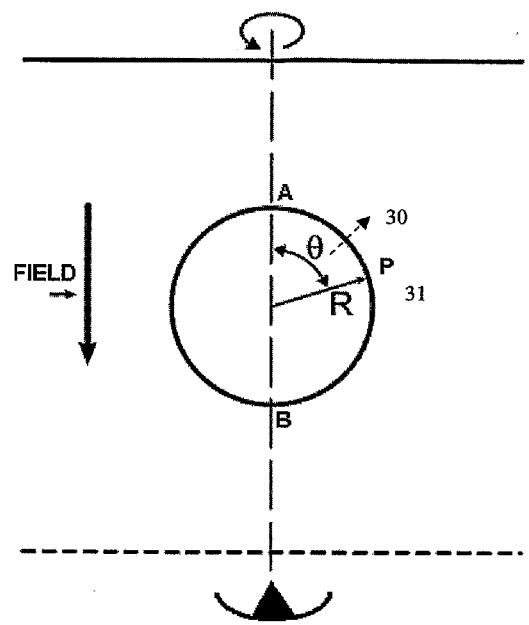
FIGURE: 3
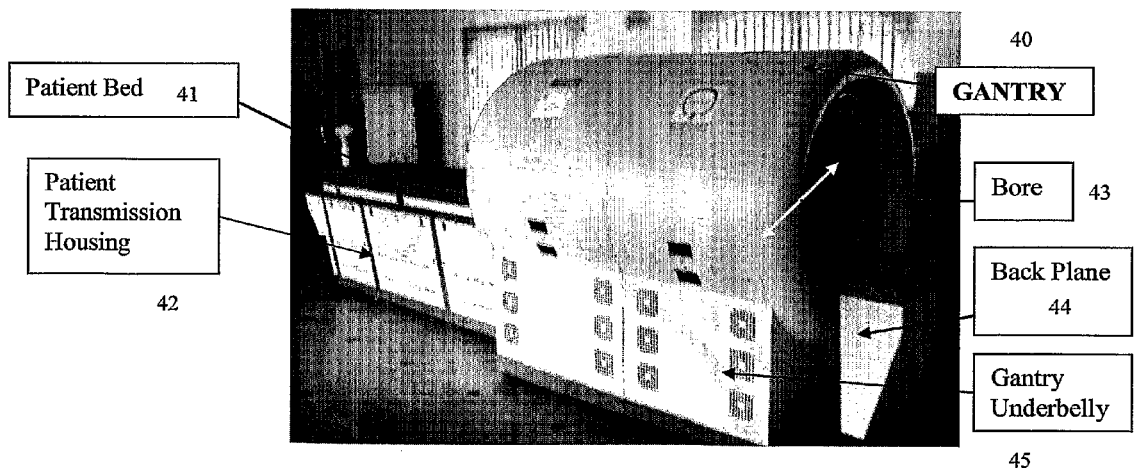
FIGURE: 4

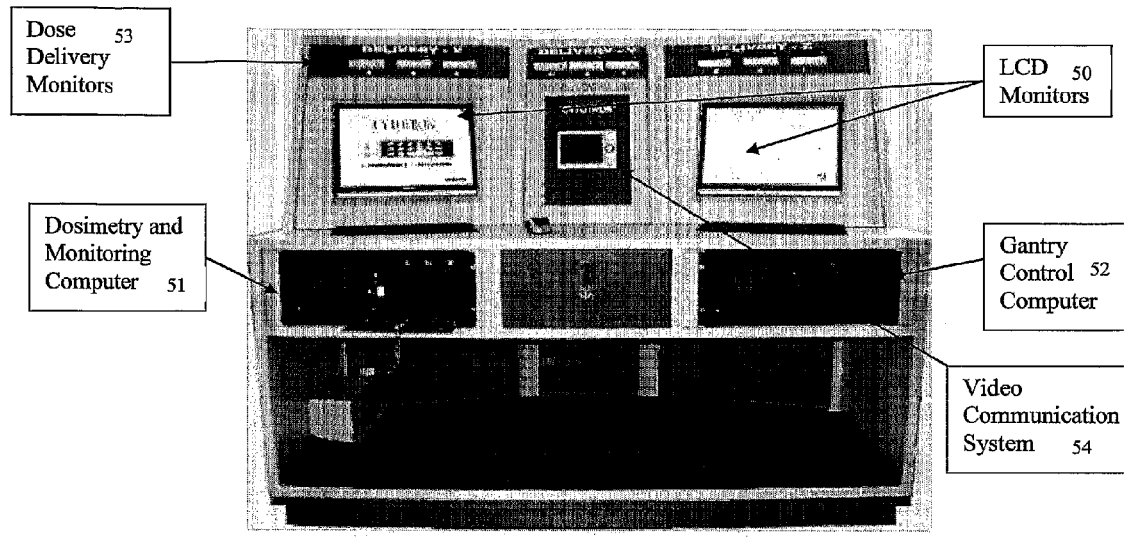
FIGURE: 5
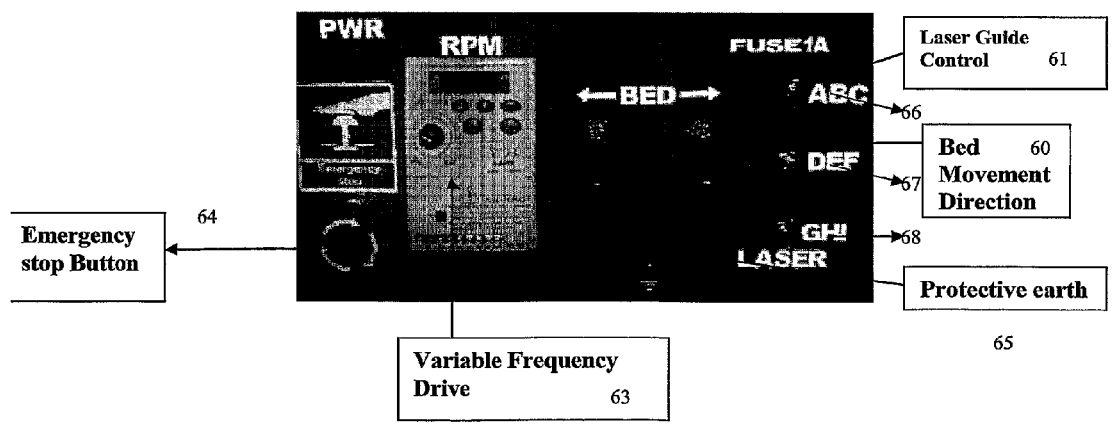
FIGURE: 6

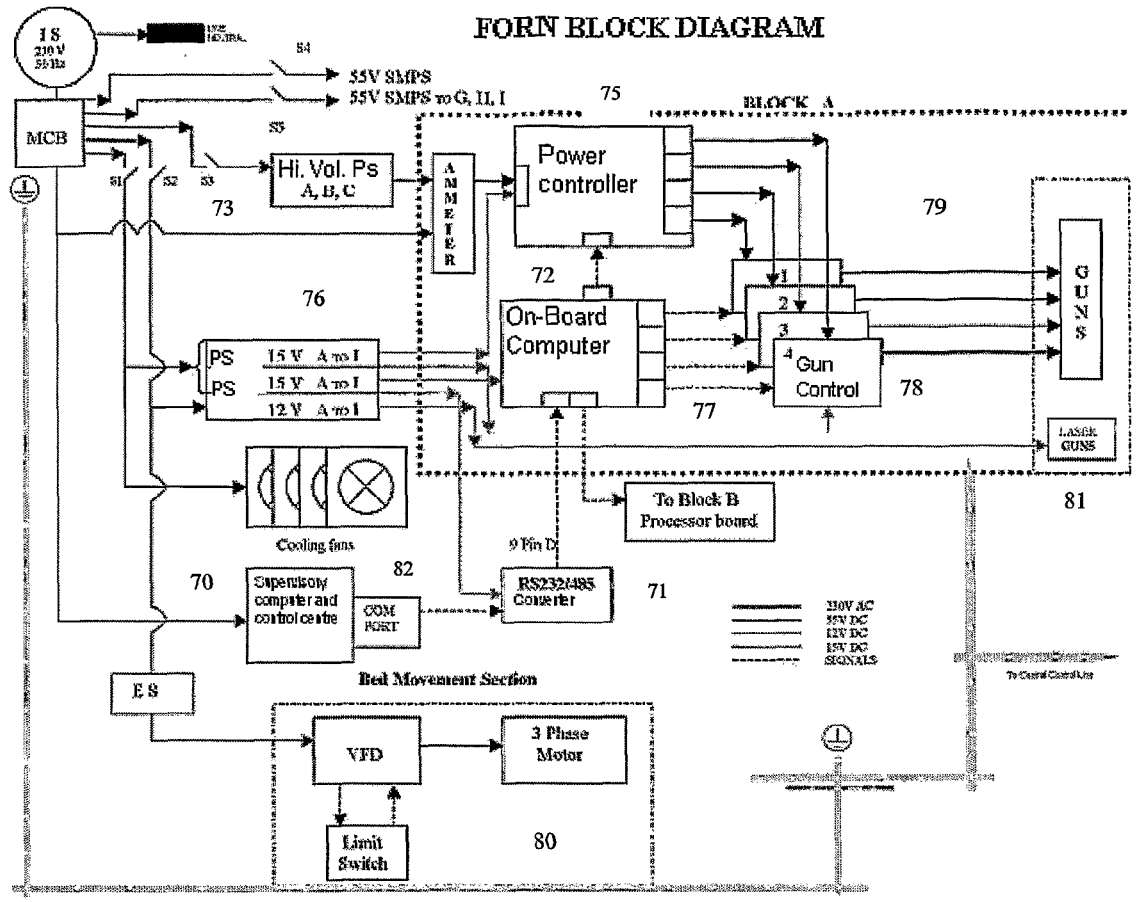
FIGURE: 7
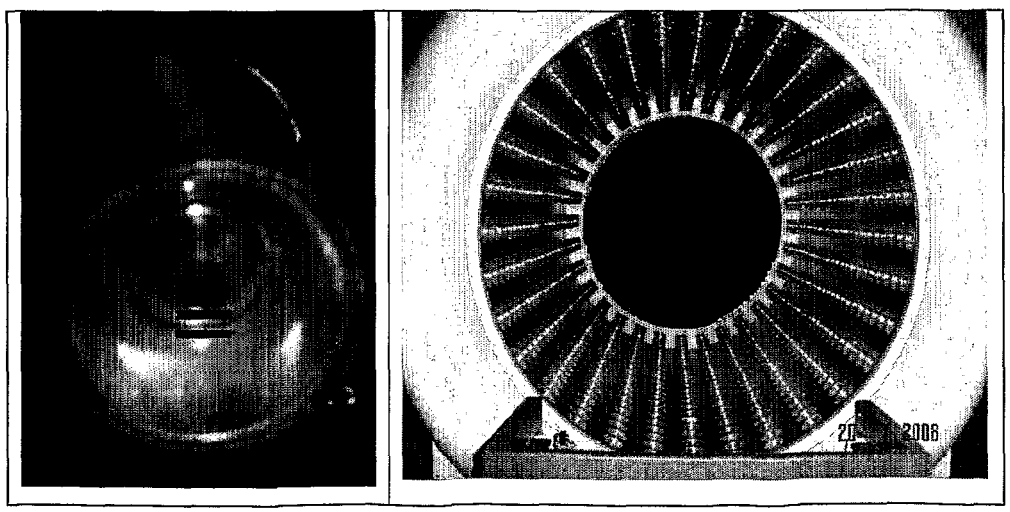
FIGURE: 8a  FIGURE: 8b

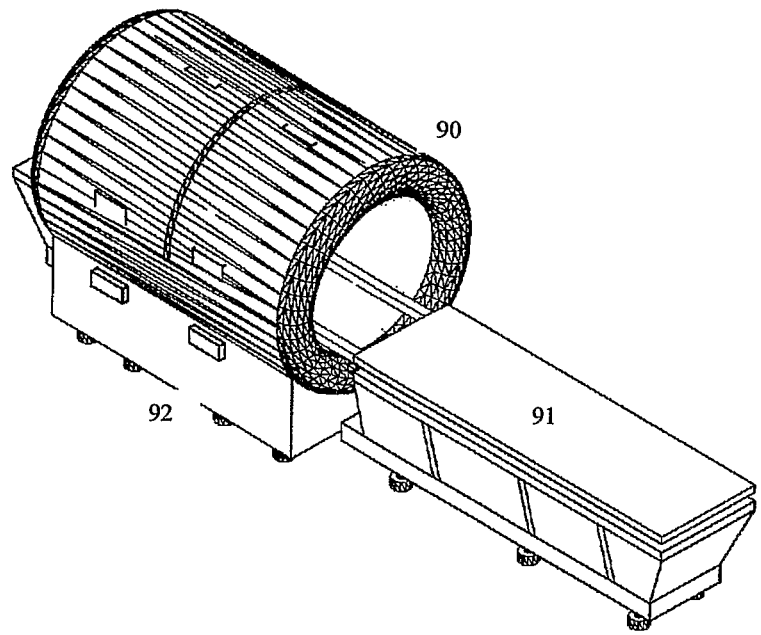
FIGURE: 9
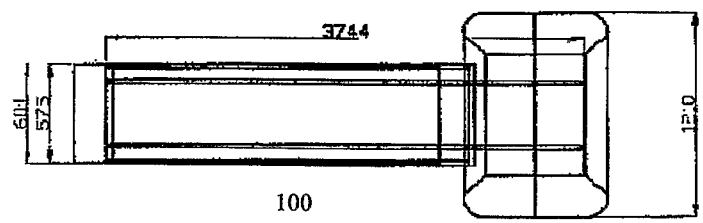
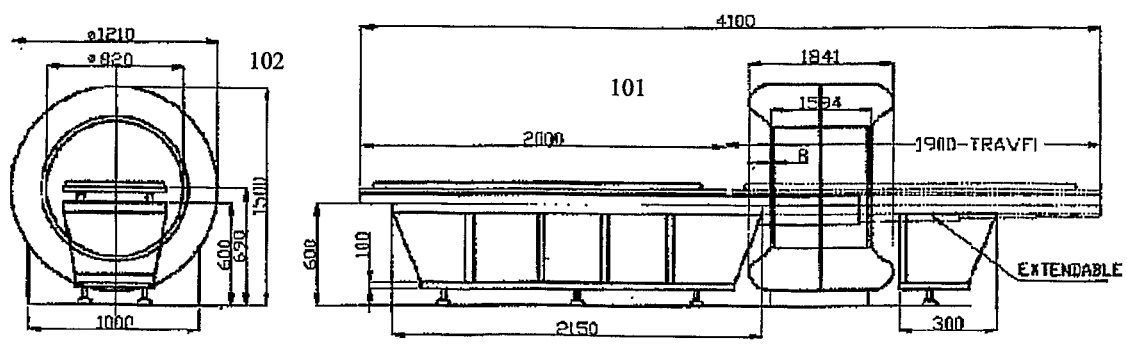
FIGURE: 10

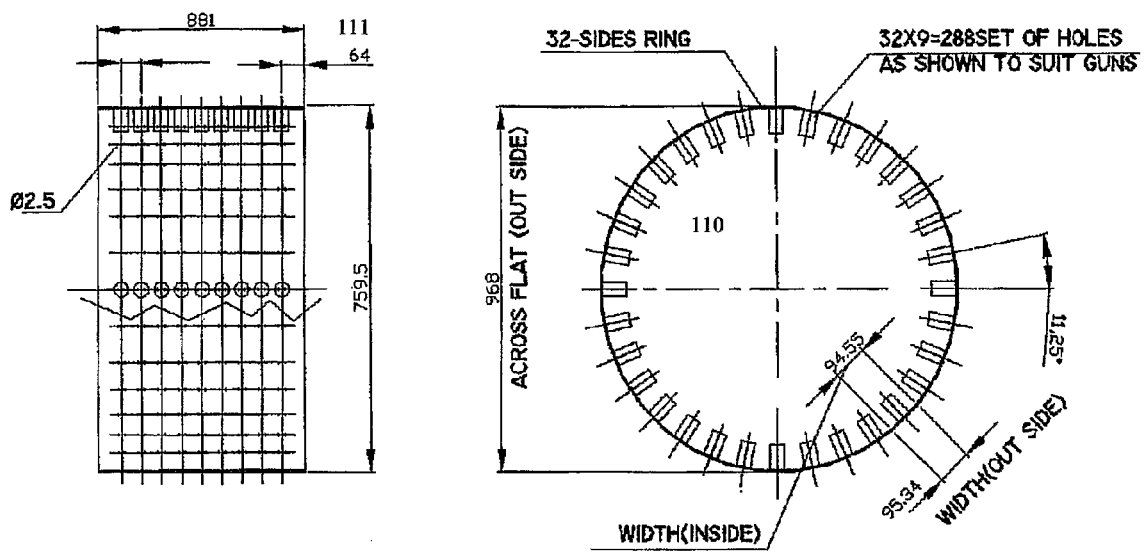
FIGURE: 11
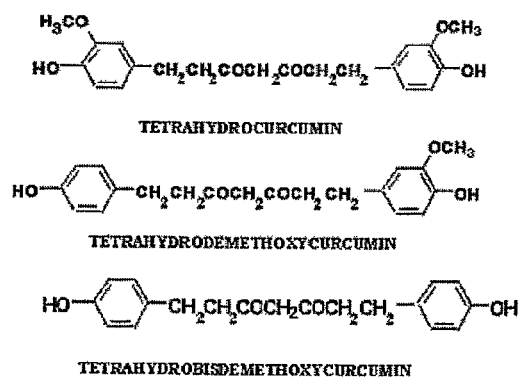
FIGURE: 12

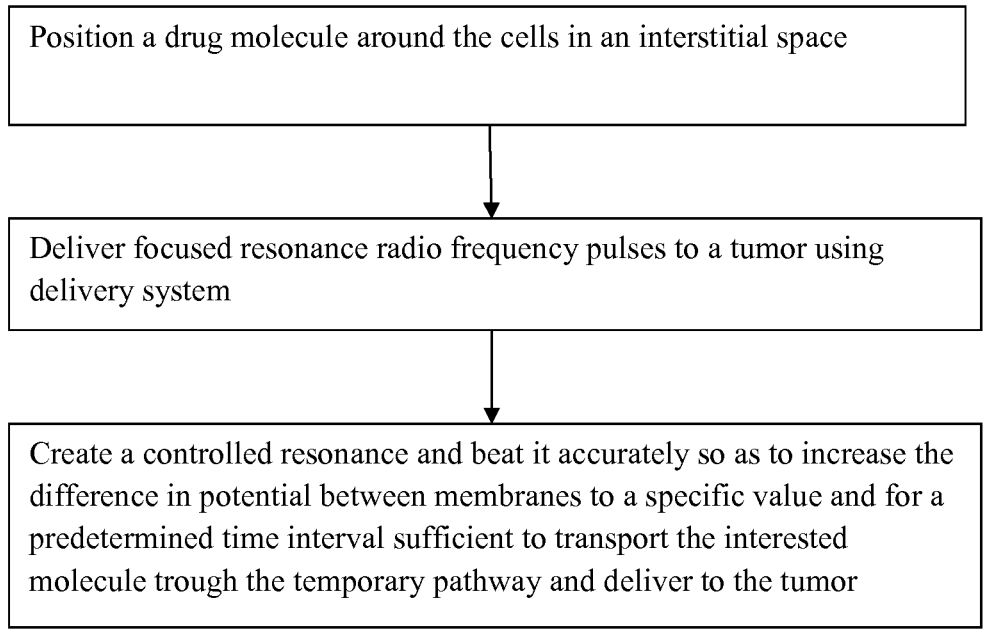
FIGURE: 13

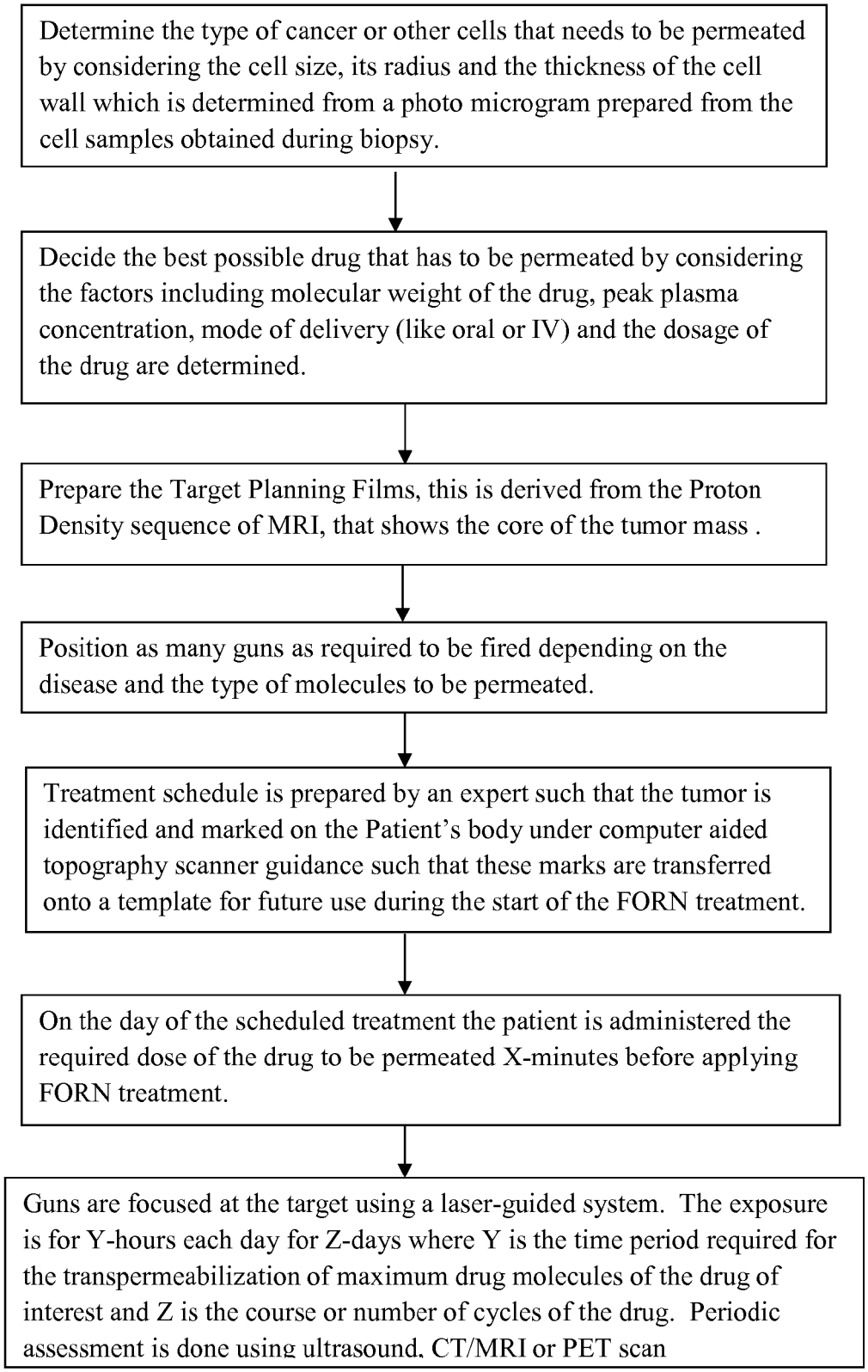
FIGURE: 14

METHOD OF TREATING CELLS WITH DRUG AND RADIATION ACCORDING TO PROTON DENSITY

The present invention relates to a method of achieving nanopermeabilization using a safe, non-invasive and highly controlled technique called Focused Resonance Nanopermeabilization (FORN).

BACKGROUND

Electric field pulses can induce the transient permeabilization. Electropermeabiliztion is a technique of using short pulses of electrical fields to cause temporary holes in the cell membrane, this is a process which is mostly done in cells in-vitro, but nanopermeabilization is a technique by which a temporary pathway is created precisely for a specific molecule based on its molecular weight. In nanopermeabilization the specific cell is resonated with high instantaneous magnetic fields and radio frequency and then the nano second signals are applied which would penetrate only the resonating cells. The present invention performs this in the cells' natural environment or in-vivo but non-invasively. Electropermeabilization is widely used for the introduction of molecules such as DNA, antibodies, enzymes, and drugs into cells. For the last ten years, it has been developed to facilitate the delivery of drugs into cancer cells in cell cultures in the laboratory. The critical intracellular target for cytotoxicity of drugs like some chemotherapy causes breaks in DNA, whereas others form DNA adducts. The cytotoxicity of drugs is dependent on their intracellular concentration, which is controlled by membrane permeability. Permeabilization of cells by electric pulses allows the hydrophilic drug to penetrate into the cells. Antitumoral drugs therefore have a direct access to the cytosol where they can fully exert their cytotoxic potential and can be used at lower doses than the ones required in classical protocols of chemotherapy. It has been shown that electroporation of cultured cells potentiates cytotoxicity of various chemotherapy agents and other targeted molecules by several hundred times. For example, the cytotoxicity of a drug called cisplatin is potentiated up to 70 times in suspended cell cultures using electric pulses in laboratory cultured cancer cells. The potentiation can be highly controlled using the present invention by adjusting delivery parameters like molecular mass of the drug, the peak plasma concentration, total tissue volume, cell membrane characteristic etc. The FORN technique can potentate the antitumor effectiveness of drugs from 10 to 70 times and can be highly localized and can be used in vivo (on tissues and organs inside the body) and non-invasively, that is, without implanting any electrodes or probes into the body of animals, plants and humans.

DISCUSSION OF PRIOR ART

U.S. Pat. Nos. 6,314,316 and 6,937,890 describe and claim a method and apparatus for delivering molecules into a target cell, and more particularly, to such methods and apparatus for achieving such delivery through electroporation.

U.S. Pat. No. 7,109,034 describes and claims a highly spatially resolved technique to alter the biochemical content of single cells and organelles, based on permeabilization of phospholipid bilayer membranes by pulsed electric fields, i.e. so called electroporation using microelectrodes that needs to be implanted directly on to the cells that needs to be treated.

U.S. Pat. No. 7,306,940 describes an electroporation device and method for delivering a modulated signal under continuous control of cell electropermeabilization.

U.S. Pat. No. 7,395,112 relates to methods of using low-strength electric fields to treat tumors. More particularly, it relates to methods and an apparatus, which utilizes low strength electric fields on the order of 20-70 V/cm, with or without adjunct chemotherapy to treat or cure various tumor and cancerous tissue, by implanting electrodes into the tumor mass to deliver electric fields. The claim uses low frequency electric pulses.

This application also draws on the patent application no. PCT/IN2004/000157 published under no. WO/2005/120171 titled "A method for tissue regeneration or degeneration in humans and an apparatus therefor", by applying rotational field narrow focused quantum magnetic resonance on the required area. The apparatus consists of a plurality of guns for delivery the quantum magnetic resonance, a traveling platform for carrying the person under treatment, an electronic switching system for controlling the guns, said electronic switching system being controlled by a main computer through an on board microprocessor and means for cooling and dispersing the heat generated during the operation.

None of the above described or known devices and methods adopt the principle of Focused Resonance Nanopermeabilization or FORN. Application of Focused Resonance Radio Frequency to the affected area or the whole body as the case may to permeate cancer drugs, vaccine, genetic materials or any other molecules of interest into the living cell of an animal, plant or human in a safe, non-invasive and controlled manner is the field of study of the present invention.

SUMMARY OF THE INVENTION

Accordingly, the primary object of the present invention is the development of a method for Focused Resonance Nanopermeabilization. A further object of the present invention is to provide an apparatus for treatment using the said method.

BRIEF DESCRIPTION OF DRAWINGS

FIG. 1 shows cell permeabilization during and after FORN treatment.

FIG. 2 shows the activities in a cell before and after FORN treatment.

FIG. 3 shows the calculation of the potential difference across the cell membrane.

FIG. 4 shows the FORN device.

FIG. 5 shows the central control unit of the FORN device.

FIG. 6 shows the features of the patient transport control.

FIG. 7 shows the block diagram of the FORN system.

FIG. 8a shows a single delivery gun with an antenna.

FIG. 8b shows the delivery system or the Gantry.

FIG. 9 shows mechanical assembly of the complete FORN device.

FIG. 10 shows mechanical assembly of the patient transmission assembly mounted with the gantry assembly.

FIG. 11 shows the gun assembly along with the mounting of the delivery guns and antenna.

FIG. 12 shows the structure of Curcumin Compounds used with FORN.

FIG. 13 is a flow chart of a method of the present invention for achieving FORN.

FIG. 14 is a flow chart of a more specific method of the present invention for achieving FORN.

DETAILED DESCRIPTION OF THE PREFERRED EMBODIMENTS

Focused Resonance Nanopermeabilization or FORN, could be defined as combined antitumor treatment that consists of systemic or local administration of cytotoxic drug (e.g. chemotherapy) followed by focused resonance radio frequency pulses delivered to the tumor or the whole body using specially designed delivery system. All cells and tissue, cancer or otherwise have a specific resonance frequency dependant on the density or concentration of hydrogen atoms in a group of these (similar) cells. When these cells are placed in a high instantaneous magnetic field, the protons in them get oriented. At this moment if a radio frequency pulse close to the resonating frequency of the cell colony is fired, these cells start attaining the beat frequency. As the frequency gets closer and closer to the resonating frequency, the resultant frequency remains constant but and the amplitude starts rising, thus increasing the transmembrane potentials many times causing temporary pathways which would close when the signal is removed after the drug passes through the cell membrane. The interesting and unique fact of this technique is that cell permeabilization occurs only in those cells or tissues (group of cells) that are in resonance and attain beat frequency. The non-resonating cells do not respond to the FORN treatment, as they are in their resting state. Consequently the main factors that play crucial roles in obtaining high responses of the FORN treatment are the drug used in the treatment and the technique and method of creating controlled resonance, and beating it accurately so as to increase the membrane potential to a specific value and for a predetermined time interval sufficient to transport the interested molecule through the temporary pathway and deliver to the tumor.

The 'ideal' drug for antitumor FORN treatment should possess at least two main properties. First, the drug should possess very high intrinsic cytotoxicity, i.e. cytotoxicity only when the drug is inside of the cells. Secondly, the drug should not cross the plasma membrane of the cell easily at physiological conditions, i.e. the highly cytotoxic drug should be non-permeant.

One of the anticancer drugs analyzed in silico was Bleomycin which exhibits both previously described properties: it is almost non-permeant and it is a potent cytotoxic when inside of the cells. Because of these properties, the cytotoxic effect of bleomycin on a FORN treated cell (or group of cells) can be increased from hundred to thousand times. An additional advantage of the use of the Bleomycin in FORN treatment is the ability of the Bleomycin to induce a larger cytotoxic effect on dividing cells in respect to non-dividing. Therefore, it brings a possibility of safe treatment of large margins around the treated tumor mass. Another good candidate as a drug for FORN treatment is Cisplatin. Translocation of this drug across the cell membrane can be facilitated by FORN and consequently increased cytotoxic activity of the drug can be obtained. Therefore, Cisplatin can be demonstrated to be also effective in FORN experiments treating various tumors in vivo, as well as in clinical trials.

FIG. 1 shows cell nanopermeabilization during and after FORN treatment. In FIG. 1, the sub-block (1) shows how the drug molecule gets aligned in the interstitial space; sub-block (2) and (3) shows the nanopermeabilization process during FORN process; sub-block (4) shows the drug been permeated into the cell through the cell membrane and the start of the reconstruction process of the cell membrane to close the nano-pore; and the sub-block (5) shows the completion of the reconstruction process and establishment of intact cell membrane after the drug has been transpermeated into the cell.

FIG. 2 shows the activities in a cell before and after FORN treatment. FORN technology is based on the fact that a spherical membrane-bound particle (20) of radius r (e.g., A cell or intracellular organelle) when placed in a plane field (21) of strength E will experience a potential difference (V) (22) across the membrane at point P which is given by;

$$V = CrE \cos \theta$$

FIG. 3 shows the calculation of the potential difference across the cell membrane. C is a constant and $\theta$ is the angle (30) made by point P (31) relative to the direction of the field (21). The maximum potential difference $V_{max}$, will therefore develop across the membrane when $\cos \theta = +1$, i.e. at points A and B as shown in FIG. 3, in line with the direction of the field.

The value of C is determined by the radius of the cell, thickness of the membrane and the relative electrical conductance of the membrane and of the fluids within and outside the cell. As might be expected, the conductance of the membrane is much smaller than that of the internal and external fluid, and the thickness of the membrane is much less than the radius of the particle, than the value of C approaches a limit of 1.5 and $V_{max} = 1.5$ r E.

Hence under such conditions the value of $V_{max}$ for a given applied field is determined by the radius of the particle. This relationship can also be expressed in another way by defining the dependence of $V_{max}$ on E for spherical particles of various radii which can be approximated with various cells and organelles. For example, exposure to a specific field will place a $V_{max}$ of 3V across the cell membrane (r=10 μm), but it will be only 30 mV across the membrane of a typical mitochondrion (r=0.2 μm). Since cell membrane breakdown occurs only when $V_{max}$ reaches the threshold voltage, selectively for localized breakdown of the cell membrane can clearly be achieved, in different cell sizes depending on the threshold of $V_{max}$. This is how selective nanopermeabilization of larger cells can be achieved while leaving the smaller cells intact. So in the environment of the cancer mass all cells are resonating, choice can be made on nanopermeabilization of different sizes of cells, this way we can even prevent damages to normal cells that are trapped in between Cancer cells.

The following are the typical steps involved in the FORN treatment of a cancer patient.

The following are the steps involved in administering the FORN treatment using a machine equipped with the FORN protocol.

1. The patient is first diagnosed for cancer using the conventional methods. A biopsy is done to establish the type of cancer cells and their morphology.
2. A MRI of the affected region or a whole body MRI is done depending on the type and severity of the disease. The proton density of each of the tumor mass all over the body is obtained using a PD (Proton Density) sequence from a magnetic resonance imaging device.
3. The radiologist and the oncologist will decide on the primary site of the cancer, and decide on planning the treatment regime, that is, the tumor to be exposed to FORN treatment.

4. The type of cancer or other cells that needs to be permeated will be carefully studied. The cell size, its radius and the thickness of the cell wall is determined from a photo microgram prepared from the cell samples obtained during biopsy.
5. The Oncologist will decide the best possible drug that has to be permeated. The molecular weight of the drug, peak plasma concentration, mode of delivery (like oral or IV) and the dosage of the drug are determined.
6. The radiologist will then prepare the "Target Planning Films", this is derived from the PD (Proton Density) sequence of MRI, that shows the core of the tumor mass and then he will position as many guns as required to be fired depending on the disease and the type of molecules to be permeated. A specially trained medical doctor then prepares the required treatment schedule from the data obtained from the oncologist and the radiologist. The tumor is identified and marked on the patient's body under computer aided topography scanner guidance. These marks are transferred onto a template for future use during the start of the FORN treatment.
7. On the day of the scheduled treatment the patient is administered the required dose of the drug to be permeated X-minutes before applying FORN treatment. (X=peak time taken (in minutes) for the drug to attain maximum concentration in the circulation in the patient).
8. On the day of the exposure, the patient is made to lie down on the machine and is rolled in; the RF-guns are now focused at the target using a laser-guided system.
9. The exposure is for Y-hours each day for Z-days. Y is the time period required for the transpermeabilization of maximum drug molecules of the drug of interest and Z is the course or number of cycles of the drug. Periodic assessment is done using ultrasound, CT/MRI or PET scan.

FORN Treatment in Immunization and Disease Prevention.

One of the promising applications of FORN is in immunization and disease prevention. Most often, it is observed that a specific molecule has to be transpermeated into the cellular system for various purposes.

Most common molecules generally needed to be transpermeated are DNA, protein, antibodies, vaccines and heavy molecules for disease prevention especially in non-communicable diseases.

It is possible to use FORN to transpermeate any molecule whose molecular weight, peak plasma concentration and washout time is known. It is important that the proton density of the tissue to which transpermeation is required is obtained, as these are the factors that are primarily required to plan the FORN process. FORN can also be performed on the whole body by using the whole body resonance frequency whereby a particular molecule of interest can be transpermeated into all the cells of the body to correct or prevent a global systemic disorder. One such example is a possible prevention of malignancy in high-risk individuals by use of the Curcuminoid molecules. Curcumin a compound commonly found in the biological source from *Curcuma Longa* (common name Turmeric), having a linear formula $[HOC_6H_3(OCH_3)CH=CHCO]_2CH_2$, with a molecular weight of 368.38. Curcumin is a natural phenolic compound. It is a highly potent anti-tumor agent having anti-inflammatory and anti-oxidant properties and is known to induce apoptosis (programmed cell death) in cancer cells and inhibits phorbol ester induced protein kinase C (PKC) activity. It is reported to inhibit production of inflammatory cytokines by peripheral blood monocytes and alveolar macrophages. It is a potent inhibitor of EGFR tyrosine kinase and IkB kinase. It also inhibits inducible nitric oxide synthase (iNOS), cycloxygenase and lipoxygenase. This wonder compound cannot only prevent malignancy in high-risk population but also correct some of the cellular mutations in patients with malignant disorders. The only problem and challenge faced today by researchers working on this compound is the bioavailablity inside the cell. This problem can be solved by FORN where this natural compound, which is highly hydrophilic, can be safely transpermeated into the cells, anywhere in the body or the whole body.

The Apparatus for Conducting FORN.

The apparatus designed for FORN is a variant of the earlier invention of the same inventor "A METHOD FOR TISSUE REGENERATION OR DEGENERATION IN HUMAN AND AN APPARATUS THEREFOR", referred to above. The new invention has substantial and significant new developments over and above what has been described in the earlier patent. The new invention shall be called "Focused Resonance Nanopermeabilization" (FORN).

FIG. 4 shows the FORN device externally consists of a large tunnel like construction called "the gantry" (40) and a long table that holds the patient bed (41). The gantry houses the special RFQMR delivery guns and the patient transmission system housing (42) is located below the bed (41) which transports the patient into the bore of the gantry (43). The back plane (44) is the end part of the device; it houses some of the safety devices. Gantry underbelly (45) is the space under the gantry, which is effectively used to place various electronic sub-systems.

FIG. 5 shows the central control unit (CCU) controls the entire operation of the device. The CCU consists of two powerful industrial computers, (all two are powerful computing devices), two touch screen high performance LCD monitors (50), a video communication system (54) and dose delivery monitors (53).

Dosimetry and Monitoring Computer.

Dose delivery and monitoring computer (51) (DMC) is used to prepare the dosimetry for patients whose treatment has to be planned. The DMC can work independently from that of the other sub-assemblies on the CCU. Planning and preparation of dose will not affect the control of the gantry and thus does not affect the patient undergoing the treatment on the FORN device.

Gantry Control Computer.

The gantry control computer (52) (GCC) is the main supervisory computer that controls all functions relating to the operation of the gantry and all its guns. The GCC also handles communication between different axes and controls the delivered dose.

Dose Delivery Monitors.

There are nine dose delivery monitors (DDM) (53); these monitors indicate the delivered dose and firing of all guns. DDMs are divided into three sets each and are named "Delivery X", "Delivery Y" and "Delivery Z" each of these are subdivided into axis A to Axis I. These DDMs also indicate if any of the guns in any of the axis is not firing.

Video Communication System.

The videl communication system (VCS) (54) is essential to communicate to the patient taking treatment inside the gantry of the Cytotron device. This is a two way audio communication and one-way video communication system. This system enables the operator to monitor the patient continuously as well as give any instruction to the patients during the treatment time.

Patient Transport Control.

FIG. 6 shows the patient transport control (PTC), which is a very important part of the device. This system has control switches (60) to control the movement of the bed (41), the speed of transport of patient, the direction of the bed movement and the control of laser guiding system (61). The variable frequency drive (63) is used to control the speed of the movement of the bed (41) into and out of the gantry. The emergency button (64) is used in case, of any malfunction of the transmission system. A protective earthing (65) is also provided for safety purposes. The laser guide control (61) is used for targeting the anatomical region of the patient that requires the treatment. The switches (66), (67) and (68) are the switches that are used to power ON the electronics relating to the nine axes A to I.

The electronics of the FORN device uses the highest design criteria and standards. The design caters to all the appropriate safety and interlocks during operations.

Explanation of the Block Diagram of the FORN System Shown in Figure Above.

FIG. 7 shows the FORN system consists of the following sub-systems:
1. Supervisory computer and control center (70).
2. On-Board computer for axis control system (72).
3. High current (76)/high voltage (73) power supply sub-assembly.
4. Power controller sub-assembly (75).
5. High speed switching sub-assembly called gun control (78).
6. Patient transport control system (80).
7. Laser guiding and focus system (81).
8. Delivery guns with parabolic antenna (79).
9. Cooling system (82).

Supervisory Computer and control center (70) is the master control of the entire system. It is here that all treatment related computation is done. The system processes MRI information to obtain the proton density of the tissue to be treated. The required inputs like molecular weight, peak plasma concentration, total washout time, tissue volume and the thickness of the cell membrane for computing the dosimetry is fed into this computer. The supervisory computer and control center is connected to the on board axis control computer and communicates via a RS232 communication protocol (71). The supervisory also keeps track of the patients' data.

On-Board computer for Axis Control System (72) receives all information relating to the dose of the patient and controls all other sub-assemblies of the FORN system. The On-Board computer also has all the necessary intelligence to takeover control if the main control system fails during treatment secession. It also controls the entire power controller (75) and the switching sub-assemblies. This sub-assembly receives the commands from the main computer (70) pertaining to the dose such as resonant frequency, wave front frequency, spin frequency applied field strength, modulation details and the rate of change of the membrane potential required for a particular patient and his treatment schedule. This information is computed and made suitable by this On-Board computer and is transmitted to other sub-assemblies for the smooth and coordinated operation of the entire system.

High current (76)/high voltage (73) power supply (HCHV) is a sub-assembly that takes in the AC 230 volts power from the mains and converts into various high voltage low current as well as high current low voltage power sources for the operation of various sub-assemblies as well as the FORN guns. This sub-assembly is the energy source for the entire system. This power supply works in the switched mode and also provides excellent isolation, withstanding a dielectric breakdown in the order of 4 Kv.

Power Controller sub-assembly (75) receives the power from the HCHV power supply and controls the distribution of the same to the various other sub-assemblies under the command and control of the On-Board computer and axis control system (72). It also takes care of the safety aspects, like over loads, temperature or thermal shutdown etc. for the safe running of the system.

High speed switching sub-assembly also called as field rotator sub-assembly (78) (HSS) receives multiple inputs from signal modulators, RF amplifiers and field rotators and operates under the command and control of the On-Board computer and axis control system (72). The HSS sub-assembly is capable of handling high voltages and currents and switch them on and off at very high frequencies, thus is capable of producing fine modulated pulses of millionth of a second. This sub-assembly directly fires the QMR guns (79), under the instruction and regulation of the On-Board computer and axis control system (72).

Signal modulator sub-assembly (77) is an important sub unit of the On-Board computer and axis control system (72). It receives multiple commands from the On-Board computer and axis control system and modulates them producing a unique quantum RF pulse that is supplied to the HSS sub-assembly (78) for firing.

The field rotator sub-assembly (78) receives rotational information from the On-Board computer and axis control system (72) and this is also an integral part of the On-Board computer and sends it to the HSS sub-assembly for the control of field rotation. Both field rotators and signal modulators play an important role in the finally achieving the desired resonance.

Delivery guns with parabolic antenna (79) are special antenna devices, made of high permeability material that produces high instantaneous magnetic field and RF pulses. There are in total 864 guns that are placed at 3×32 configuration at a resolution of 11.25 degrees. There are three delivery systems known as "delivery X", "delivery Y", and "delivery Z", each of these delivery systems consists of 3 axes totaling to 9 axes in total. These guns are accurately focused at the target tissue at the time of treatment. 864 independent switching devices drive these guns from the HSS sub-assembly. FIG. 8A shows the complex assembly of the delivery guns.

Patient transport control system (80) is that part of the machine that accurately positions the patients on the bed inside the bore of the gantry of the FORN machine. This sub-system consists of motors, drives and gearbox for the purpose of smooth and efficient control.

Laser guiding and focus system (81) is used for focusing the emissions of the guns precisely to the effected part of the body. The patient gets a marking on the surface of the body under which the tissue to be treated is located. The marking is done using the computerized tomography (CT). The patient's part of the body to be treated is placed inside the bore of the gantry of the FORN device and the laser guides are turned on. A final adjustment of the patient transmission system is done to obtain precise focusing.

Cooling system (82) is intended to cool the machine so it functions within its operating temperature range. Temperature control is very important as the delivered signal can change its characteristics when there is a large temperature variation. The cooling system is based on heat conduction away from the source of the heat and a forced air, cools the heat conduction system.

Mechanical Design.

As explained earlier, the FORN device is a huge mechanical construction which is critical to its functioning. The mechanical system is critically designed to provide not only the convenience of using the device both for the operator and the patient but functionally it provides for efficient heat transfer, minimize stray radiation from the device. The dimensions and design of the mechanical system also plays an important role in its overall operation.

FIG. 9 shows the mechanical assembly of the complete FORN device. This device can also perform the functions of Rotational Field Quantum Nuclear Magnetic Resonance (RFQMR) as well as Focused Resonance Nanopermeabilization (FORN). The materials used in the mechanical assembly is are aluminum alloy, aluminum castings and steel of various grades.

The critical mechanical components consist of the following;
1. Gantry bore and gun assembly (90)
2. Patient transmission assembly (91)
3. Bore and gun mounting assembly (92)

FIG. 10 shows the mechanical assembly of patient transmission assembly mounted (100) with the gantry assembly (101). The device is capable of accommodating the complete human body.

FIG. 11 shows the gun assembly; the figure shows the mounting of the delivery guns (110) and antenna (111). The gun is precisely mounted such that the device software meant for its functioning takes into account the positions of the guns in space for the various calculations of radiated emission, transmission and propagation.

Summary of Clinical Cases.

Case Study 1.

FORN Mediated Metronomic Chemotherapy.

Synopsis.

Standard chemotherapeutic drugs, when modified by the frequency and dose of administration, can target angiogenesis (growth of new blood vessels). This approach is referred to as antiangiogenic chemotherapy, or metronomic chemotherapy.

Angiogenesis, the process by which tumors induce new blood vessels for continued growth and spread, has attracted increasing attention (ever since Folkman's original hypothesis). His model of cancer-mediated angiogenesis contained several novel predictions. First, growing tumors require an expanding blood supply to obtain nutrients and oxygen as well as to remove waste products, a process mediated by inducers of angiogenesis. Second, tumor cells are genetically unstable and mutate rapidly to overcome therapy. In contrast, endothelial cells (cells lining the inside of blood vessels) are under normal cellular command and control and thus lack the ability to become drug-resistant. Third, prolonged therapy would be required to maintain suppression of neo-vascularization. Since Folkman's initial observation, many angiogenesis pathways have been identified and have provided novel targets for clinical intervention. Newly developed drugs have focused on targeting angiogenesis by altering cytokines (e.g., VEGF), altering the molecular environment in which angiogenesis occurs (e.g., matrix-metalloproteinases [MMPs]), or attacking the cells needed to populate vascular growth (i.e., endothelial cells). Both synthetic drugs and naturally occurring proteins are undergoing clinical testing as single agents or in combination with standard treatment (chemotherapy or radiation therapy). The first major clinical trial of an angiogenesis inhibitor (bevacizumab [Avastin]) showing significant activity has been reported. Waiting for additional novel antiangiogenic drugs to become available and tested in appropriate combinations will take many more years, even though therapies are required now. Most chemotherapeutic drugs used to target proliferating tumor cells have well-defined mechanisms of action and toxicities, raising the question of whether these same drugs could also target proliferating cells important in angiogenesis, including endothelium, pericytes, and circulating endothelial precursors. The standard chemotherapy, given over 3 to 5 days, can kill dividing endothelial cells, it has little sustained antiangiogenic activity during the 3- to 4-week rest periods needed for organ recovery (usually bone marrow and gastrointestinal). During this recovery phase, the few endothelial cells that had been killed are more than made up for by aggressive endothelial proliferation. Thus, although traditional chemotherapy has some antiangiogenic effects, it is ineffective at the intermittent schedules used. The antiangiogenic activity is achieved only after waves of endothelial cell apoptosis occurred did tumor cell death ensue. It is also interesting that unlike tumor cells, which easily become resistant to repeated doses of a drug, endothelial cells appeared to be a stable target, as predicted by the original hypothesis. The activity and mechanism of antiangiogenic chemotherapy has been confirmed in animal studies using different chemotherapy agents. Recently, the mechanism by which metronomic chemotherapy mediates some of the antiangiogenic effect has been reported to be via increasing thrombospondin-1 levels in animals. These preclinical metronomic chemotherapy experiments raise the question of whether a similar effect could be achieved clinically in patients.

One such patient RZ aged 9 years; a patient of recurrent Meduloblastoma, the patient RZ presented in the Europe in January 2007, with headaches and emesis, and subsequently developed a gait abnormality. A brain MRI on 15 Jan. 2007, revealed a posterior fossa lesion that was resected on 19 Jan. 2007. Pathology revealed medulloblastoma. Post-operatively RZ developed right CN 6 and 7 palsies, nystagmus and ataxia. Staging work-up revealed her to have standard-risk disease. On 19 Feb. 2007 an Ommaya reservoir was placed without complication.

RZ was confirmed on a study in the US on 26 Feb. 2007. Between 28 Feb. 2007 and 3 Jul. 2007, she received intra-Ommaya 131-I-3F8 radioimmunotherapy without complication. From 12 Mar. 2007 to 20 Apr. 2007, she received protocol-prescribed reduced-dose external beam radiation therapy (1800 cGy craniospinal, IMRT boost to the tumor bed and 1 cm margin to 5400 cGy). From 14 Mar. 2007 to 16 Apr. 2007, she also received the first 5 of 8 planned weekly doses of vincristine. She returned to her home country in Europe from the US on 22 Apr. 2007. She then received care as per MSKCC 02-088 from doctors in her home country. She completed her protocol of the treatment on 4 Feb. 2008, well tolerated.

RZ had a routine surveillance brain MRI on 27 Aug. 2008, when she was doing very well, but that unfortunately showed recurrent disease in the bilateral frontal horns of the lateral ventricles. A spine MRI was performed on 9 Feb. 2008 and on 9 May 2008, doctors informed RZ's parents that CSF cytology obtained from RZ's Ommaya confirmed the presence of recurrent disease. They started RZ on temozolomide on 30 Aug. 2008.

A radiology review was made on the 27 Aug. 2008, a brain MRI was obtained and on 2 Sep. 2008 a spine MRI obtained at the pediatric neuro-oncology tumor board. The board confirmed the bilateral lesions in the frontal horns of the lateral ventricles. Though any unequivocal lesions on the spine MRI would be appreciated, but the neuro-radiologists felt that their interpretation was qualified because they would have preferred that additional sequences be included in the radiological study. Unfortunately on the 27 Aug. 2008, brain MRI and the Ommaya CSF cytology revealed recurrent tumor (19 months post-diagnosis).

The patient then decided for the metronomic chemotherapy. During the first leg, the patient was put on three anti angiogenic drugs and two chemotherapy drugs Cyclophosphamide and VP 16, altered every three weeks in metronomic mode. After 2 weeks of the treatment, the patient had severe bone marrow depression and her blood counts went so low that she needed a blood transfusion. She also had high-grade fever. The chemotherapy was stopped for a week and given a blood transfusion and stabilized the patient. In the second leg the patient was then put on FORN mediated metronomic chemotherapy upon the request of her father. The first drug to be transpermeated was Cyclophosphamide, which has a molecular weight of 279.10, for the remaining one-week, then the drug was switched with Etoposide VP16, which has a molecular weight of 588.60, for the next 3 weeks.

During the period of FORN mediated metronomic chemotherapy, the patient did not have any discomfort, the blood counts were normal, cerebrospinal fluid examination did not show any tumor cells. The patient put on 3 kgs of weight during the 28 days of treatment. Since one course of FORN is 28 days, the patient preferred to take a break for three weeks due to personal and domestic reasons. The patient left to her country in Europe. During the FORN break period, as advised by the patient's treating oncologist, the patient continued the chemotherapy without FORN. Thus during the third leg the patient took chemotherapy without FORN. One week from stop of FORN, the patient started to get weaker, loss of appetite, and had fever. A blood test confirmed that her blood counts have again gone down, like a situation before FORN. Another transfusion of blood was conducted.

This proves that when cytotoxic drug was given to a cancer patient during the first leg of treatment, it caused a lot of adverse side effects leading to loss of weight, loss of hairs, loss of appetite, bone marrow depression and fever. The same drug at the same dose administered with FORN during the second leg did not give any adverse side effects, on the contrary reversed all of the adverse effects previously caused by the cytotoxic drugs during first leg without FORN. During the third leg of the trial, the cytotoxic drugs were continued to be administered, without the use of FORN. The adverse side effects returned almost in the same intensity as before, seen in the first leg of the treatment. The above case history proves that, FORN technology can be used to provide maximum bioavailablity of drugs, especially to the cancer cells in treatment of cancer and preventing toxic drugs to cause large-scale collateral damage to other normal cells in the body.

Case Study 2;

FORN Mediated Transpermeabilization of Therapeutic Molecules into the Living Cells A male volunteer patient, KV, aged 55 years, was diagnosed with nasopharyngeal carcinoma (head and neck cancer), four months ago. A biopsy confirmed the diagnosis. The patient was declared inoperable, which is common in most of the cancers of this type. There was no chemotherapy offered to him and the patient had refused ionizing radiotherapy. This patient presented with bulged eye, severe pain, loss of sight in the left eye, hearing loss in the left ear, loss of speech and loss of balance. The patient was given 28 exposures of RFQMR a treatment based on an earlier invention of the same inventor. The patient had come for the review after one month post exposure, magnetic resonance imaging scans taken 30 days after the RFQMR treatment showed that the tumor was not progressing, the balance was regained, and he was totally out of pain. The inventor had come across a paper that spoke of a natural substance called Curcumin that can suppresses growth of head and neck tumor cell lines in the lab *[Curcumin Suppresses Growth of Head and Neck Squamous Cell Carcinoma; Clin. Cancer Res.* 2005; 11(19) Oct. 1, 2005]. Curcumin is a compound commonly found in the biological source from *Curcuma Longa* (common name Turmeric), having a linear formula $[HOC_6H_3(OCH_3)CH=CHCO]_2CH_2$, with a molecular weight of 368.38. Curcumin is a natural phenolic compound. The anti-tumor properties of Curcumin are discussed earlier in this specification. The inventor obtained three potentially powerful anticancer curcuminoids extracted from Indian Turmeric. Their structure and formula is given in FIG. 12.

These are rather heavy molecules and biopenetrations into tumor cells are difficult. FORN was used to transpermeate the above molecules into the cancer cells of this patient.

The protocol followed in this case was as follows: 65 mg/kg during the first week; 97 mg/kg for the second week; 65 mg/kg during the third week; and 97 mg/kg again during the fourth week. FORN was started 70 minutes after the patient has orally taken the drug with a water-soluble fat as a vehicle, to achieve maximum plasma concentration of the drug.

Every day 60 minutes of FORN was induced, and scheduled for 28 consecutive days. Within the first four sessions the patient could talk, he got his lost speech back; swelling in the left eye has significantly reduced. The patient has put on one-kilogram weight. After one month a repeat biopsy will be conducted to assess the damages to the cancer cells.

FORN can successfully be used to transpermeate specific beneficial molecule through the cell membrane of living cells, in the aim of achieving therapeutic benefits in cancer and other diseases.

The invention claimed is:

1. A method of treating cells in a patient in need of treatment of the cells, comprising the steps of:
   i) determining a proton density of tissue comprising the cells;
   ii) contacting the cells with a drug selected according to a feature selected from a group consisting of molecular weight, peak plasma concentration, and washout time; and
   iii) treating the cells and the drug with radio frequency electromagnetic radiation at a resonance frequency selected according to the determined proton density of the tissue comprising the cells for a duration sufficient to allow the drug to enter the cells,
   wherein the resonance frequency is selected so as to create a temporary pathway through the cell membrane and is applied to the cell membrane for a predetermined time interval sufficient to transport the drug molecule through the temporary pathway and into the cell, and
   wherein the drug is administered in the circulatory system of the patient for a sufficient period of time prior to treating the cells with the radio frequency electromagnetic radiation whereby the drug has attained a maximum concentration within the circulatory system of the patient being treated with the drug, and the cells and the drug are treated with the radio frequency electromagnetic radiation for a time period each day equal to a half-life period of the drug in the circulatory system of the patient for a therapeutically acceptable course of the drug.

2. The method according to claim 1, wherein the cells are cancer cells.

3. A method of treating a mass of cancer cells in a human in need of treatment of the mass of cancer cells comprising:
   i) determining a resonance frequency of a radio frequency electromagnetic radiation with which to treat the mass of cancer cells;
   ii) determining a dose of a cancer drug, wherein the cancer drug is selected according to a feature selected from a group consisting of molecular weight, peak plasma concentration, and washout time in the human's circulatory system;
   iii) administering the dose to the human's circulatory system; and
   iv) focusing electromagnetic radiation on the mass of cancer cells for a time sufficient to optimize delivery of the cancer drug inside the cancer cells,
   wherein the resonance frequency is selected so as to create a temporary pathway through a cell wall of the cancer cells and is applied to the cell wall of the cancer cells for the time sufficient to allow the cancer drug to permeate the cell wall of the cancer cells and enter the cancer cells, and
   wherein the cancer drug is administered to the human's circulatory system for a sufficient period of time prior to the focusing of electromagnetic radiation, whereby the cancer drug has attained a maximum concentration within the human's circulatory system, and the cancer cells and the cancer drug are treated with the radio frequency electromagnetic radiation for a time period each day equal to a half-life period of the cancer drug in the human's circulatory system for a therapeutically acceptable course of the cancer drug.

4. The method according to claim 3, wherein the dose of the cancer drug is sufficient to attain a maximum concentration of the cancer drug contacting the cancer cells.

5. The method according to claim 4, wherein the cancer drug is selected from the group consisting of a DNA molecule, a protein, an antibody, a vaccine, a cytotoxic drug, and a curcuminoid.

* * * * *